United States Patent [19]

Raleigh et al.

[11] Patent Number: 5,674,693
[45] Date of Patent: Oct. 7, 1997

[54] DERIVATIVES OF 2-NITRO-IMIDAZOLES AS HYPOXIC CELL MARKERS

[75] Inventors: James Arthur Raleigh; David Yue-Wei Lee, both of Chapel Hill, N.C.

[73] Assignee: Natural Pharmacia International Inc., Research Triangle Park, N.C.

[21] Appl. No.: 214,520

[22] Filed: Mar. 18, 1994

[51] Int. Cl.$^6$ .................... G01N 33/574; G01N 33/554
[52] U.S. Cl. ................... 435/7.23; 435/960; 436/63; 436/64; 436/519
[58] Field of Search .................. 435/7.23, 960; 436/519, 63, 64

[56] References Cited

U.S. PATENT DOCUMENTS

| | | | |
|---|---|---|---|
| 4,241,060 | 12/1980 | Smithen | 546/210 |
| 4,282,232 | 8/1981 | Agrawal | 546/210 |
| 4,797,397 | 1/1989 | Suto et al. | 546/113 |
| 5,086,068 | 2/1992 | Raleigh et al. | 536/27 |

OTHER PUBLICATIONS

C. E. Smithen et al., Radiat. Sensitizers: Their Use Clin. Manage. Cancer [Proc. Conf.](1980), Meeting date 1979, pp. 22–32, Editor: L. Brady. Novel(nitro–1–imidazolyl)– alkanolamines as potential radiosensitizers with improved therapeutic properties.

R.C. Urtasun et al., Br. J. Cancer (1986) vol. 54, pp. 453–457. (1986).

Raleigh et al., Br. J. Cancer, vol. 69, 1994, pp. 66–71. (1994).

Chapman, "Medical Intelligence", vol. 301, No. 26, pp. 1429–1432. (1979).

Raleigh et al., Br. J. Cancer, vol. 56, 1987, pp. 395–200. (1987).

*Primary Examiner*—Mary E. Ceperley
*Attorney, Agent, or Firm*—Millen, White, Zelano, & Branigan, P.C.

[57] ABSTRACT

Derivatives of 2-nitro-imidazole, such as 1-(2-hydroxy-3-piperidinopropyl)-2-nitro-imidazole, are useful as hypoxic cell markers for immunochemical detection of hypoxia in tumor tissue.

11 Claims, 1 Drawing Sheet
(1 of 1 Drawing(s) in Color)

DERIVATIVES OF 2-NITRO-IMIDAZOLES AS HYPOXIC CELL MARKERS

BACKGROUND OF THE INVENTION

1. Field of the Invention

This invention relates to certain derivatives and corresponding optical isomers of 2-nitro-imidazole compounds, such as 1-(2-hydroxy-3-piperidinopropyl)-2-nitroimidazole, useful as hypoxic cell markers for immunochemical detection of hypoxia in tumor tissue.

2. Description of the Prior Art

Hypoxic cells are most commonly found in tumors. Within solid tumors, cells can be chronically hypoxic because of limited diffusion of oxygen from blood vessels, or they can be acutely or transiently hypoxic because of intermittent blood flow. Although cells deprived of oxygen and nutrients ultimately die, a tumor may possess viable hypoxic cells that are still functioning. These hypoxic tumor cells are more resistant to radiation therapy. It has been determined that the rate of killing by radiation is 2.5 to three times higher for aerobic cells close to the blood supply than cancerous cells which are hypoxic. Hence hypoxic cells are more likely to survive radiation or chemotherapy and because they remain viable, eventually lead to the reappearance of the tumor [J. D. Chapman, Current concepts in cancer, New Engl. J. Med., 301: 1429–1432 (1979)]. The present invention provides a measure of tumor hypoxia by immunochemical detection of a novel class of hypoxic cell markers. The methodology according to the present invention provides a convenient and cost-effective technique for measuring the degree of hypoxia in tumors, so that therapeutic interventions which are designed to deal with the presence of hypoxia in the tumors can be selected in an effective and timely fashion.

It has been known since 1970 that certain nitroaromatic compounds will metabolically bind to hypoxic cells. A variety of techniques have been developed based on this discovery to determine the presence of hypoxic cells in living tissue [Raleigh, et al., An enzyme linked immunosorbent assay for hypoxia marker binding in tumors, Br. J. Cancer., 69: 66–71 (1994)]. One way of identifying and quantifying hypoxic tissue in tumors is by the use of radioactively labeled 2-nitroimidazoles. The radiochemical is injected into tumor bearing animals or humans. The excess chemical is allowed to wash out and biopsy samples are measured by scintillation counting and autoradiography [Urtasun et al., A novel technique for measuring human tissue $pO_2$ at the cellular level., Br. J. Cancer, 54: 453–457 (1986)]. This approach can provide important information on the degree of tumor hypoxia, but is not generally acceptable because of the stringent requirements associated with handling radioactive tissues and body fluids. Nevertheless, the studies with radioactively labeled drugs have established the usefulness and feasibility of the overall concept.

Agrawal, U.S. Pat. No. 4,282,232, discloses nitroimidazoles as useful in radiosensitizing hypoxic cells. The compounds are administered to sensitize hypoxic cells for radiation treatment. Further examples of the use of nitroimidazoles in this manner is disclosed in Smithen, U.S. Pat. No. 4,241,060. These patents, which include the synthesis of 2-nitroimidazole compounds, are all centered around the sensitization of hypoxic cells for radiation treatment and do not disclose the use of these compounds as hypoxic cell markers for immunochemical detection of tumor hypoxia. Furthermore, the 2-nitroimidazoles are synthesized and used in the art as racemic mixtures. Neither stereoselective synthesis of the R and S enantiomers, nor recognition that the enantiomers respond differently to hypoxic cells, is disclosed.

More relevant is Raleigh et al., U.S. Pat. No. 5,086,068, which discloses that the binding of 2-nitroimidazoles to protein carriers in vitro is a useful method in preparing immunogens for the production of antibodies. However, Raleigh, et al. do not recognize that the enantiomers of 2-nitroimidazoles with side chains such as 1-(2-hydroxy-3-piperidinenopropyl)-2-nitroimidazole, respond differentially to monoclonal antibodies reagents raised to detect these compounds bound to macromolecules in hypoxic cells [Raleigh et al., Development of a fluorescence immunohistochemical analysis for hypoxic cells in spheroids and experimental tumors,., Br. J. Cancer, 56: 395–400 (1987); Raleigh et al., An enzyme linked immunosorbent assay for hypoxia marker binding in tumors., Br. J. Cancer, 69: 66–71 (1994)]. The present invention is an improvement over that of the Raleigh et al. patent, in that it provides improved hypoxic cell markers.

SUMMARY OF THE INVENTION

It is a principle object of the present invention to provide an improved method for immunochemical detection of tumor cell hypoxia. Another object of the present invention is to provide a novel class of hypoxic cell markers which are synthesized enantiomerically. The sensitivity and specificity of the detection is enhanced by enantiomeric recognition of the monoclonal antibody specific to these chiral hypoxic cell markers. Still another object of the present invention is to increase the uptake of these hypoxic cell markers in tumors by introducing a spacer and a basic substituent group onto the side chain.

It has been discovered that 2-nitroimidazole derivatives of the following general formula I are advantageous as hypoxic cell markers:

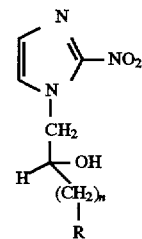

wherein:

a) n=1–6,

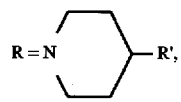

where R'=H, $NH_2$, OH, $CH_2OH$ or $NR''_2$ ($R''=CH_3$, $C_2H_5$), or b) n=1–6,

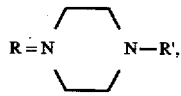

where R'=H, alkyl (1–6 carbon atoms), $CH_2OH$, piperidinyl, piperazinyl, or a substituted aromatic group, or physiologically acceptable salts thereof.

The enantiomers of these compounds are represented, for example, by the following formulae II for 1-(2-hydroxy-3-piperidinopropyl)-2-nitroimidazole:

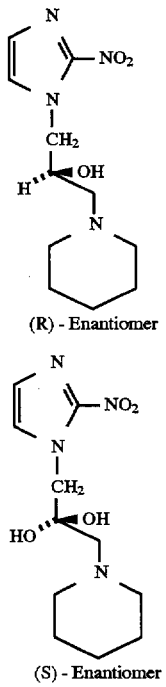

In addition to the enantiomeric recognition by the monoclonal antibody, the compounds of the present invention with a basic piperidinyl or piperazinyl group would have an advantage of increased uptake in hypoxic tumor cells. The spacer (n=6) inserted between the chiral center and the basic substituent would enhance the antibody recognition of the chiral hypoxic cell marker.

Upon further study of the specification and appended claims, further objects and advantages of this invention will become apparent to those skilled in the art.

A more complete appreciation of the invention and many of the attendant advantages thereof will be readily obtained by reference to the following detailed description.

DETAILED DESCRIPTION OF THE INVENTION

According to this invention, an improved immunochemical method is provided for detecting hypoxic tissue and cells in tumors and other living matter. A feature of the present invention is based on the discovery that the above-described compounds of the present invention, such as 1-(2-hydroxy-3-piperidinopropyl)-2-nitroimidazole, metabolically bind preferentially to hypoxic tissue rather than to normal oxygenated tissue. Furthermore, it has been discovered that the S enantiomer of 1-(2-hydroxy-3-piperidinopropyl)-2-nitroimidazole is 5–10 times better as a competitive inhibitor of monoclonal antibody binding to solid phase antigen than is the racemic mixture. The special properties of the S enantiomer of 1-(2-hydroxy-3-piperidinopropyl)-2-nitroimidazole and its derivatives make them a preferred embodiment of the invention.

The enantiomers may be synthesized, for example, by reacting 2-nitroimidazole with R or S epichlorohydrin in the presence of a catalytic amount of potassium carbonate to form the corresponding R or S chlorohydrin derivative of 2-nitroimidazole. Refluxing the chlorohydrin derivatives dissolved in absolute ethanol containing an excess of piperidine, produces the desired products as the free base [R'=piperidinyl]. Acidification with hydrogen chloride gas followed by evaporation of the solvent provides the hydrochloride salts of the chiral free bases. An alternative route to the R and S enantiomers of 1-(2-hydroxy-3-piperidinopropyl)-2-nitroimidazole include the stereoselective reduction of 1-(2-keto-3-piperidinopropyl)-2-nitroimidazole with chiral reducing agents. Enantiomers of the other compounds of formula I may be synthesized in an analogous manner.

As previously noted, the administration of the selected 2-nitroimidazoles to animals or humans results in the metabolic binding of the nitroaromatic compounds to hypoxic tissue in tumors. The specific binding is thought to be due to the presence of enzymes which interact with the chiral 2-nitroimidazoles on a three dimensional basis. The enantiomers of a racemic drug often differ in pharmacodynamic and pharmacokinetic properties as a result of stereoselective interaction with chiral macromolecules [Ariens et al., Eur. J. Clin. Pharmacol., 26, 663 (1984); Drayer, et al., Clin. Pharmacol. Ther., 40, 125 (1986)]. The desired pharmacological effect is often associated with only one of the enantiomers in a racemic mixture. For instance, (+)-ketamine is the predominately responsible for an hypnotic effect whereas the (−)-isomer is the main source of side effects [White, et al., Anesthesiology, 52, 231 (1980)].

2- Nitroimidazoles have been studied extensively as hypoxic cell radiosensitizers. Its clinical applications however, are limited by the development of central and peripheral neuropathies. The compounds of present invention bearing a basic piperidinyl or piperazinyl group as hydrochloride salts significantly improve water solubility and tumor uptake. Although the main object of this invention is on the method of detection hypoxia in tumors, we recognize that these compounds may also be used as cytotoxic agents for treating hypoxic tumor cells.

The administration of the chiral 2-nitroimidazoles to a tumor-bearing patient results in the nitroreductase activity leading to binding of the drug to the hypoxic tissue. A biopsy sample of the patient's tumor is taken for purposes of investigation by use of the antibodies developed by Raleigh et al, U.S. Pat. No. 5,086,068, which describes the general methodology for the inventive method, and is incorporated by reference herein. For example, at a predetermined time prior to analysis of a tumor, e.g., 20 hours prior to surgical inspection of the tumor by, e.g., biopsy, the tumor bearing animal or patient is administered the hypoxic cell marker by injection. An administration dosage to provide a whole body concentration of 5–150 micromolar is preferred. The tumor sample taken is then analyzed according to the invention. The chiral 2-nitroimidazole compounds administered to the patient are the same compound which are used as haptens in producing antibody reagents. As a general overview of the process, the biopsy sample of the tumor may be fixed in cold ethanol at 0°–20° C. for histological examination including light microscopy, fluorescence microscopy or electron microscopy. Alternatively or in addition, a sample of the fresh tissue can be weighed, homogenized and analyzed by enzyme linked immunosorbent assay [ELISA, Raleigh, et al., Br. J. Cancer, 69: 66–71 (1994)]. Finally, a fresh biopsy sample can be enzymatically digested and made into a single cell suspension for analysis by flow cytometry. In each case, specific antibodies which recognize the nitroimidazole compounds bound to the hypoxic cells are used as the primary analytical reagents. In each case the analysis is conducted according to standard techniques of immunohistology, ELISA or flow cytometry. In each case, and as suitable, standard immunochemical detection schemes incorporating commercially available secondary immunochemical reagents can be used including but not limited to fluorescence-labeled, enzyme-labeled and ferritin-labeled or gold labeled secondary antibodies. Standard image and flow cytometric analyses are performed on the tumor samples to estimate the extent of tumor hypoxia in the tumor samples and to relate this to therapy outcome and/or the presence of other physiological factors which might affect therapy outcome.

Other features of the invention will become apparent in the course of the following descriptions of exemplary embodiments which are given for illustration of the invention only and are not intended to be limiting thereof.

The entire disclosure of all applications, patents and publications, cited above are hereby incorporated by reference.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

EXAMPLES

Figure 1:
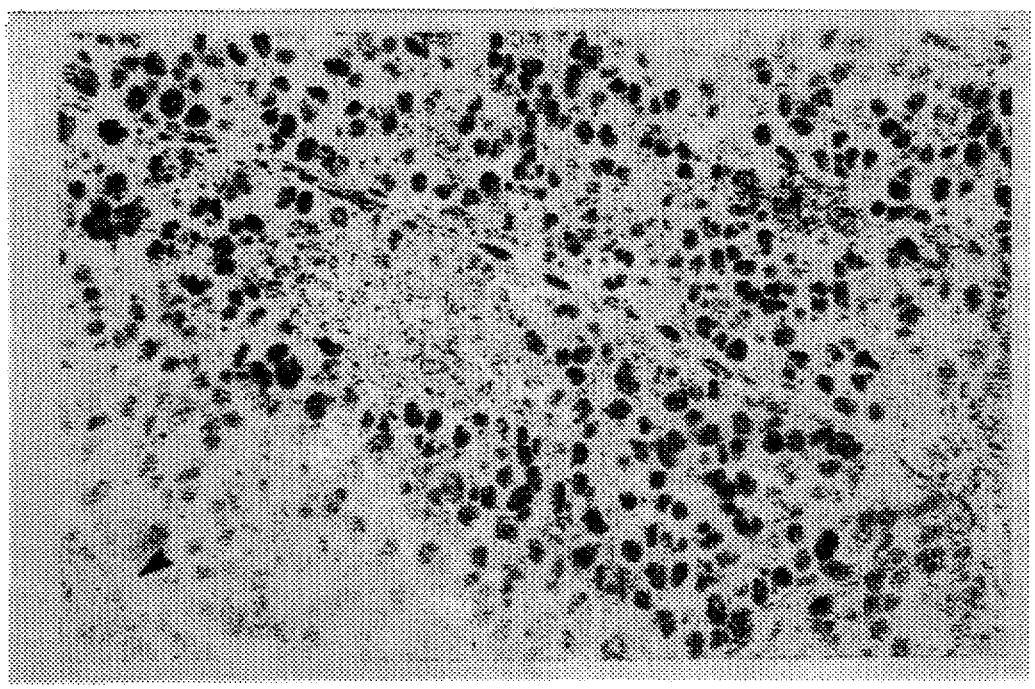
FIG. 1 shows the immunostaining of the tissue section of a C3H mammary adenocarcinoma labelled in vivo with racemic 1-(2-hydroxy-3-piperidinopropyl)-2-nitroimidazole (Magnification×400). Immunostaining is observed in cells distant to tumor vasculature [arrow] as expected of hypoxic tumor cells. Sections such as these can be used to quantify the extent of tumor hypoxia in terms of the ratio of labelled cells to total cells in the sections.

Example 1.—Synthesis of R and S enantiomers of 1-(2-hydroxy-3-piperidinopropyl)-2-nitroimidazole.

To 1.15 gram of 2-nitroimidazole in 20 mL of absolute ethanol was added 100 mg of potassium carbonate and 1.0 gram (R)-epichlorohydrin. The reaction mixture was refluxed overnight. The cooled reaction mixture is added to 150 mL of saturated aqueous sodium chloride containing 5% sodium bicarbonate. The reaction mixture was extracted with ethyl acetate (3×10 mL) and the organic extract was dried over anhydrous sodium sulfate, filtered and concentrated to give 1.87 gram of the R enantiomer of 1-(2-hydroxy-3-chloropropyl)-2-nitroimidazole. A similar reaction procedure starting with (S)-epichlorohydrin gives 1.45 gram of the S enantiomer.

The chiral intermediate was reacted with a four fold excess of freshly distilled piperidine in 25 mL of refluxing absolute ethanol for 16 hours. The reaction mixture was evaporated to dryness, the solid residue was taken up in 25 mL water, and acidified with 2N HCl. The solution was washed with dichloromethane (3×15 mL). The aqueous layer was basified with 2N sodium hydroxide solution and extracted with dichloromethane (3×15 mL). The organic extract was dried over anhydrous sodium sulfate, filtered and concentrated to give a pale yellow solid of the R or S enantiomers of 1-(2-hydroxy-3-piperidinopropyl)-2-nitroimidazole. The hydrochloride salts of the respective R and S enantiomers were prepared by means of dissolving the free bases in ethanol and treating with a slight excess of alcoholic hydrogen chloride.

Example 2—ELISA with R and S 1-(2-hydroxy-3-piperidinopropyl)-2-nitroimidazole

In ELISA studies according to literature procedure [Raleigh, et al., Br. J. Cancer., 69: 66–71 (1994)], it was shown that the S enantiomer of 1-(2-hydroxy-3-piperidinopropyl)-2-nitroimidazole was 5 to 10 times better as a competitive inhibitor of monoclonal antibody binding to solid phase antigens than was the racemic mixture. For these studies, the solid phase antigen for coating the ELISA plates consisted of racemic 1-(2-hydroxy-3-piperidinopropyl)-2-nitroimidazole reductively bound to thiolated Ficoll by the radiation chemical technique used to bind the same compound to BSA.

Example 3—Oxygen dependence of 1-(2-hydroxy-3-piperidinopropyl)-2-nitroimidazole binding to mammalian cells in tissue culture.

For the determination of the oxygen dependence of binding of 1-(2-hydroxy-3-piperidinopropyl)-2-nitroimidazole to hypoxic cells, EMT6 cells suspended at $10^{-6}$ cells/mL in 25 mL of phosphate buffered saline (PBS) were placed in a series of silanized 125 mL gas collection tubes which were thoroughly washed with distilled water and autoclaved before use. The cell suspensions were equilibrated with gas phases containing varying amounts of oxygen by means of repeated gas exchanges under partial vacuum. The cells were maintained in suspension by constant agitation of the tubes on a shaker. A small volume of solution in PBS was injected into the cell suspensions to achieve a final concentration of 100 micromolar of the hypoxia marker, 1-(2-hydroxy-3-piperidinopropyl)-2-nitroimidazole. The cells were incubated for 2 hours at 37° C. after which time the cells were harvested, washed extensively and analyzed by ELISA for covalently bound hypoxia marker. The ELISA values for binding of 1-(2-hydroxy-3-piperidinopropyl)-2-nitroimidazole under different gas phase oxygen concentrations were reported relative to the maximum degree of binding achieved under anoxic conditions (<10 ppm $O_2$). The oxygen dependence of 1-(2-hydroxy-3-piperidinopropyl)-2-nitroimidazole binding to EMT6 cells in vitro showed half maximal inhibition of binding at a gas phase oxygen concentration of 0.1% which was comparable to published values of 0.1 to 0.3% for half maximal inhibition of misonidazole binding in this cell line.

Example 4—Immunohistochemistry and tumor hypoxia in experimental tumors

Antibodies to 1-(2-hydroxy-3-piperidinopropyl)-2-nitroimidazole reductively bound to proteins were used to reveal hypoxic cells in mouse C3H mammary adenocarcinomas by standard peroxidase immunostaining techniques (FIG. 1). For these experiments, C3H carcinoma cells in single cell suspension were injected into the gastrocnemius muscle of five week old male C3H mice at $10^5$ to $10^7$ cells per mouse. Tumors were investigated when they reached a diameter of 8 mm. 1-(2-Hydroxy-3-piperidinopropyl)-2-nitroimidazole was administered intraperitoneally at a concentration of 60 mg/kg mouse weight. Mice were killed after 4 hours by cervical dislocation and the tumors excised and fixed in 10% neutral buffered formalin for 24 hours. The fixed tissue was then embedded in paraffin and sectioned at

We claim:

1. In a method for immunochemical detection of tumor cell hypoxia, which comprises binding of hypoxic tumor cells with an amount of a hypoxic cell marker effective to allow immunochemical detection and detecting the bound hypoxic tumor cells immunochemically, the improvement wherein the hypoxic cell marker is of the following formula I:

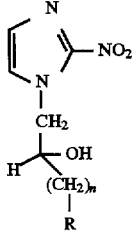

wherein:
a) n=1–6,

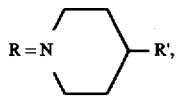

where R'=H, NH$_2$, OH, CH$_2$OH or NR"$_2$ and R"=CH$_3$, C$_2$H$_5$, or
b) n=1–6,

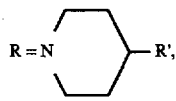

where R'=H, alkyl of CH$_2$OH, piperidinyl, piperazinyl, or a substituted aromatic group, the R group being bonded from the last CH$_2$ group in (CH$_2$)$_n$ to the free ring nitrogen atom in the R group, or physiologically acceptable salts thereof.

2. The method of claim 1, wherein said hypoxic cell marker is in the form of a hydrochloride or hydrobromide salt.

3. The method of claim 1, wherein the hypoxic cell marker is 1-(2-hydroxy-3-piperidinopropyl)-2-nitromidazole or a hydrochloride or hydrobromide salt thereof.

4. The method of claim 1, wherein the hypoxic cell marker is the S enantiomer of 1-(2-hydroxy-3-piperidinopropyl)-2-nitroimidazole, substantially free from the R enantiomer thereof.

5. The method of claim 1, wherein the hypoxic tumor cells are human hypoxic tumor cells.

6. The method of claim 1, wherein, in formula I, n is 6.

7. The method of claim 1, wherein a dosage of the hypoxic cell marker to provide a whole body concentration of 5–150 micromolar is administered to a patient as the amount effective to allow immunochemical detection.

8. In a method for immunochemical detection of tumor cell hypoxia, which comprises binding of hypoxic tumor cells with an amount of a hypoxic cell marker effective to allow immunochemical detection and detecting the bound tumor cells immunochemically, the improvement wherein the hypoxic cell marker is of the following formula I:

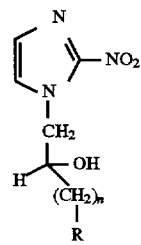

wherein the chiral side chain is in the S configuration, and wherein:

a) n=1–6,

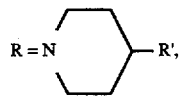

where R'=H, NH$_2$, OH, CH$_2$OH or NR"$_2$ and R"=CH$_3$, C$_2$H$_5$, or b) n=1–6,

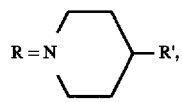

where R'=H, alkyl of 1–6 carbon atoms, CH$_2$OH, piperidinyl, piperazinyl, or a substituted aromatic group, the R group being bonded from the last CH$_2$ group to the free ring nitrogen atom in the R group, or physiologically acceptable salts thereof.

9. The method of claim 8, wherein the hypoxic cell marker is substantially free from the R enantiomer of formula I.

10. The method of claim 8, wherein said hypoxic cell marker is in the form of a hydrochloride or hydrobromide salt.

11. In a method for immunochemical detection of tumor cell hypoxia, which comprises binding of hypoxic tumor cells with an amount of a hypoxic cell marker effective to allow immunochemical detection and detecting the bound tumor cells immunochemically, the improvement wherein the hypoxic cell marker is of the following formula I:

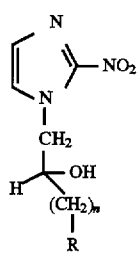
wherein:
a) n=1–6,
where R'=H, NH$_2$, OH, CH$_2$OH or NR''$_2$ and R''=CH$_3$, C$_2$H$_5$, or
b) n=1–6,
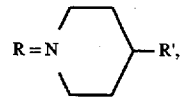
where R'=H, alkyl of 1–6 carbon atoms, CH$_2$OH, piperidinyl or piperazinyl, the R group being bonded from the last CH$_2$ group to the free ring nitrogen atom in the R group, or
physiologically acceptable salts thereof.
* * * * *